(12) United States Patent
Da Cruz (10) Patent No.: US 12,329,672 B2
(45) Date of Patent: Jun. 17, 2025

(54) ORTHODONTIC/ORTHOPAEDIC DEVICE AND METHOD

(71) Applicant: Joseph Da Cruz, Queanbeyan (AU)

(72) Inventor: Joseph Da Cruz, Queanbeyan (AU)

(*) Notice: Subject to any disclaimer, the term of this patent is extended or adjusted under 35 U.S.C. 154(b) by 691 days.

(21) Appl. No.: 17/535,051

(22) Filed: Nov. 24, 2021

(65) Prior Publication Data

US 2022/0160532 A1 May 26, 2022

(30) Foreign Application Priority Data

Nov. 24, 2020 (AU) .............................. 2020904345

(51) Int. Cl.

| | | |
|---|---|---|
| *A61F 5/058* | (2006.01) | |
| *A61C 7/08* | (2006.01) | |
| *A61C 7/10* | (2006.01) | |
| *A61C 7/36* | (2006.01) | |
| *A61C 19/045* | (2006.01) | |
| *A61C 19/05* | (2006.01) | |
| *B29D 99/00* | (2010.01) | |
| *A61C 9/00* | (2006.01) | |
| *B29K 33/04* | (2006.01) | |

(52) U.S. Cl.
CPC ............ *A61F 5/05891* (2013.01); *A61C 7/08* (2013.01); *A61C 7/10* (2013.01); *A61C 7/36* (2013.01); *A61C 19/045* (2013.01); *A61C 19/05* (2013.01); *B29D 99/00* (2013.01); *A61C 9/00* (2013.01); *B29K 2033/04* (2013.01)

(58) Field of Classification Search
CPC ......... A61F 5/05891; A61C 7/08; A61C 7/10; A61C 7/36; A61C 19/045; A61C 19/05; A61C 19/04; A61C 19/00; A61C 7/00; B29D 99/00; B29K 2033/04
USPC ........................................................ 433/68
See application file for complete search history.

(56) References Cited

U.S. PATENT DOCUMENTS

| | | | | |
|---|---|---|---|---|
| 7,134,874 B2* | 11/2006 | Chishti | .................. | A61C 9/00 |
| 2015/0136147 A1* | 5/2015 | Lucas | ..................... | A61C 7/08 |
| | | | | 128/861 |

FOREIGN PATENT DOCUMENTS

| | | | | |
|---|---|---|---|---|
| WO | WO-9641584 A1 * | 12/1996 | .............. | A61C 7/00 |
| WO | WO-2005032396 A1 * | 4/2005 | .............. | A61C 7/10 |
| WO | WO-2022076795 A1 * | 4/2022 | .............. | A61F 5/08 |

* cited by examiner

*Primary Examiner* — Ralph A Lewis
*Assistant Examiner* — Mirayda A Aponte
(74) *Attorney, Agent, or Firm* — Oliff PLC (57) ABSTRACT

A method of preparing a device. The method includes fitting the device onto a first jaw of a patient, the device having a platform contoured for contact with teeth of the first jaw, identifying a set of contact areas between the device and teeth of a second jaw of the patient when the first and second jaws are moved towards each other, shaping, adjusting and/or trimming the device on the basis of the set of contact areas to change a location of at least one contact area, and repeating the preceding steps to bring the contact areas to or towards a desired configuration.

25 Claims, 10 Drawing Sheets

ORTHODONTIC/ORTHOPAEDIC DEVICE AND METHOD

FIELD OF THE INVENTION

The invention relates generally, but not exclusively, to methods and devices for use in orthopaedic/orthodontic correction to alter muscle function, facial and dental development, pain, headaches and migraines of primary origin. Examples of the invention relate to adjusting the position of the jaw and the teeth to create/improve muscle relaxation, sleep, breathing, posture, growth and development and increased muscle strength.

The entire content of patent application No. 2004277278 is hereby incorporated in its entirety by reference thereto.

BACKGROUND TO THE INVENTION

Some people suffer from chronic pathologies, such as temporomandibular joint disorder, atlas and axis subluxation, sleep disorders, breathing disorders and cranial distortions. Without wishing to be limited by theory, the inventor has found that the proprioception of the teeth perceived by the brain has an effect on the motor response of the head and neck muscles. Hence, corrections to teeth and jaw alignment may result in muscle relaxation and a reduction in detrimental signal patterns between the brain, teeth, muscles and associated structures. Specifically, it has been observed by the inventor that the signal response of muscles during clenching and bruxing are modulated when rest and translational jaw positions are varied. When the occipital condyles are balanced with the fossae of atlas and posterior teeth, a great deal of release occurs in the cranio cervical junction. Such changes may generate more favourable signal patterns, which results in muscle relaxation, observable by greater range of rotational motion of the head, wider jaw opening and softer patient muscles observed on palpation, and increased strength, which has been verified with resistance muscle testing.

Furthermore, encouraging forward movement of the jaw may increase space behind the patient's tongue, which can improve breathing and alleviate sleep abnormalities, reduce destructive parafunction, decrease neck pain and muscle tightness, allow lymphatic flow and decrease the size of enlarged tonsils.

The mandible can move relative to the maxilla in four different motions primarily: side to side, a hinging movement rotating downwards, a forwards and downwards translation, and a forwards and upwards rotation (also known as the counter-clockwise movement of the jaw). This counter-clockwise movement releases tension in the neck, restores TMJ joint space and, importantly, increases jaw opening and function.

Some of the misalignments/abnormalities in the patient's jaw/teeth that may cause these issues include misaligned midlines between maxilla and mandible, cant or tilt of the jaw, vertical dimension loss between jaws, and lack of balanced occlusion on left and right sides. Other misalignments/abnormalities that may occur are that the posterior teeth appear intruded and front teeth appear taller in a vertical dimension. There are 7 distinct strain patterns that occur at the sphenobasilar junction known in the art.

Examples of the invention may seek to ameliorate or at least alleviate some or all of the health concerns discussed above.

SUMMARY OF THE INVENTION

According to a first aspect of the present invention, there is provided a method of preparing a device comprising: fitting the device onto a first jaw of a patient, the device having a platform contoured for contact with teeth of the first jaw; identifying a set of contact areas between the device and teeth of a second jaw of the patient when the first and second jaws are moved towards each other; shaping, adjusting and/or trimming the device on the basis of the set of contact areas to change a location of at least one contact area; and repeating the preceding steps to bring the contact areas to or towards a desired configuration.

Preferably, identifying the set of contact areas comprises identifying a set of contact areas between the device and the second jaw of the patient when one jaw is translating horizontally and the first and second jaws are moved closer to the other ("parafunction contact areas"); and wherein at least some of the shaping, adjusting and/or trimming of the device comprises shaping, adjusting and/or trimming the device on the basis of said set of parafunction contact areas to change a location of at least one parafunction contact area.

Preferably, the horizontal translation includes one or more of forward and backward, side-to-side and circular motions.

Preferably, at least some of the shaping, adjusting and/or trimming of the devices is based on whether the translation contact areas are balanced on left and right sides of the device.

Preferably, identifying the set of contact areas comprises identifying a set of contact areas between the device and the second jaw of the patient when the first and second jaws are in a central position ("rest contact areas"); and wherein at least some of the shaping, adjusting and/or trimming of the device comprises shaping, adjusting and/or trimming the device on the basis of said set of rest contact areas, to change a location of at least one rest contact area.

Preferably, at least some of the shaping, adjusting and/or trimming of the devices is based on whether the rest contact areas are balanced on left and right sides of the device.

Preferably, at least some of the shaping, adjusting and/or trimming of the device is based on whether the parafunction and rest contact areas occur in substantially similar locations.

Preferably, the contact areas are at the desired configuration when each parafunction contact area occurs in a substantially similar location to a rest contact area and the contact areas are substantially balanced on left and right sides of the device.

Preferably, the method further comprises shaping, adjusting and/or trimming at least one of the patient's teeth to change a location of at least one contact area.

Preferably, wherein the contact areas are identified using coloured articulating paper.

Preferably, a first set of contact areas is identified using articulating paper that is coloured differently to articulating paper used to identify a second set of contact areas.

Preferably, the shaping, adjusting and/or trimming of the device is performed by using a rotary cutting tool.

Preferably, wherein the device is shaped, adjusted or trimmed to change the location(s) of posterior contact area(s) prior to shaping, adjusting and/or trimming the device to change the location(s) of one or more anterior contact area(s).

Preferably, the device, prior to any shaping, adjusting and/or trimming step, is formed in accordance with the patient's bite impression.

Preferably, the bite impression is made in alginate or rubber.

Preferably, the method further comprises forming the device around a mould of the bite impression.

Preferably, the method further comprises taking one or more measurements of a degree to which the patient's head turns left and right, a deviation of the midlines of the first and second jaws, height of jaw opening between teeth and a length of protrusion forward of the mandible in relation to a patient's maxilla in translation to determine whether the patient requires tooth or jaw correction and to monitor changes to patient physiology as the patient uses the device.

According to a second aspect of the present invention, there is provided a device prepared according to the first aspect of the invention.

Preferably, the device is made substantially from acrylic.

Preferably, the acrylic is heat cured high quality acrylic with no monomer.

Preferably, the device further comprises a two-way or three-way expansion screw configured to adjust the size of the device.

Preferably, the device defines a hole in the anterior palatal area behind a patient's front teeth in use to accommodate the patient's tongue for ease of speech.

Preferably, the anterior portion of the device is open.

Preferably, the device results in a vertical separation of the jaws of the patient or bite of up to 20 mm. More preferably, the device results in a vertical separation of the jaws of the patient or bite of between 5 and 15 mm. Yet more preferably, the device results in a vertical separation of the jaws of the patient or bite of approximately 10 mm.

A further aspect of the invention relates to use of the device in accordance with the second aspect of the invention for the provision of orthopaedic care.

BRIEF DESCRIPTION OF THE FIGURES

Embodiments of the present invention will now be described, by way of non-limiting example only, with reference to the accompanying drawings briefly described as follows.

DETAILED DESCRIPTION

Corrections to a patient's jaw may be achieved by use of an orthopaedic/orthodontic device. The inventor has found that the device generally achieves more than merely correction of teeth and typically has a wider orthopaedic effect. Accordingly, the device is referred to as an orthopaedic/orthodontic device. As used in this disclosure, "orthopaedic" includes maxillofacial orthopaedics (as well as other orthopaedic areas eg spine). Orthopaedic devices include devices for improving the skeletal structure of the patient's face and jaw, bone movement, arrangement of joints, bones, muscles, ligaments, and proprioception signalling to the nervous system. Thus, orthopaedics as used herein, encompasses the face, neck, head posture and airway. As used in this disclosure, "orthodontic" refers to the diagnosis, prevention and correction of malpositioned teeth and jaws. It also encompasses modification of facial growth, also known as dentofacial orthopaedics.

Figure 1A:
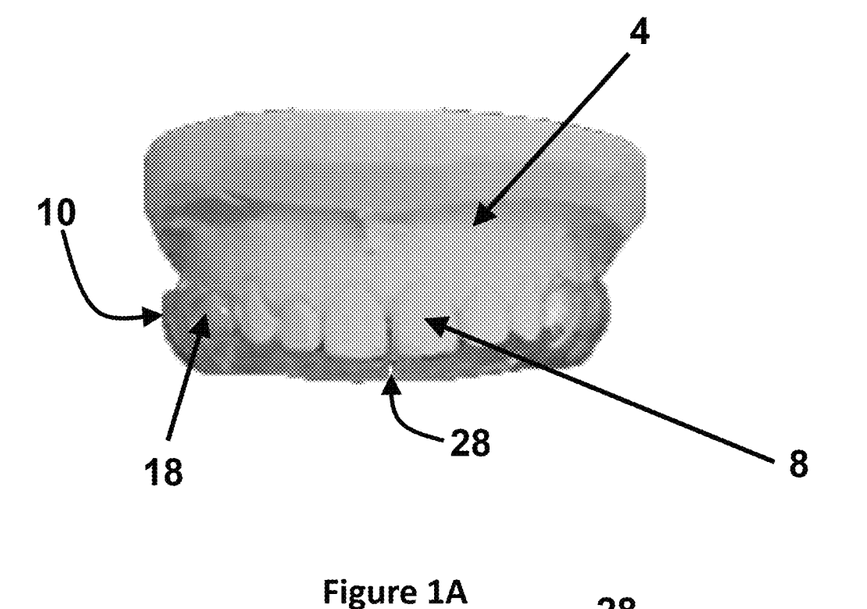
FIG. 1A is a front view of an orthopaedic/orthodontic device fitted to a plaster cast representing the maxilla of a patient.
Figure 1B:
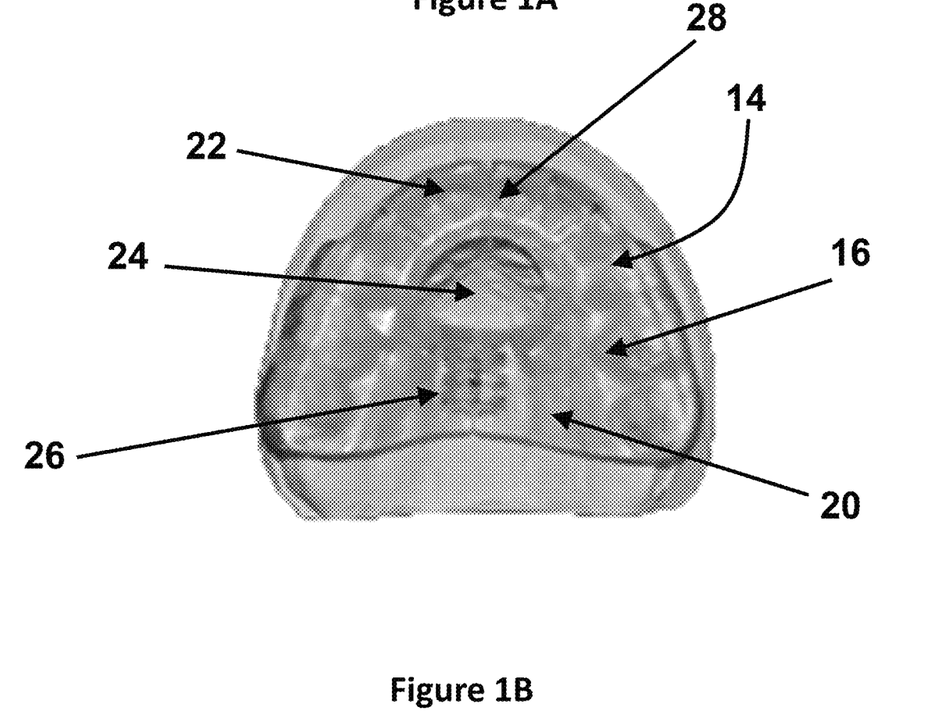
FIG. 1B is a top view of the orthopaedic/orthodontic device shown in FIG. 1A.
Figure 1C:
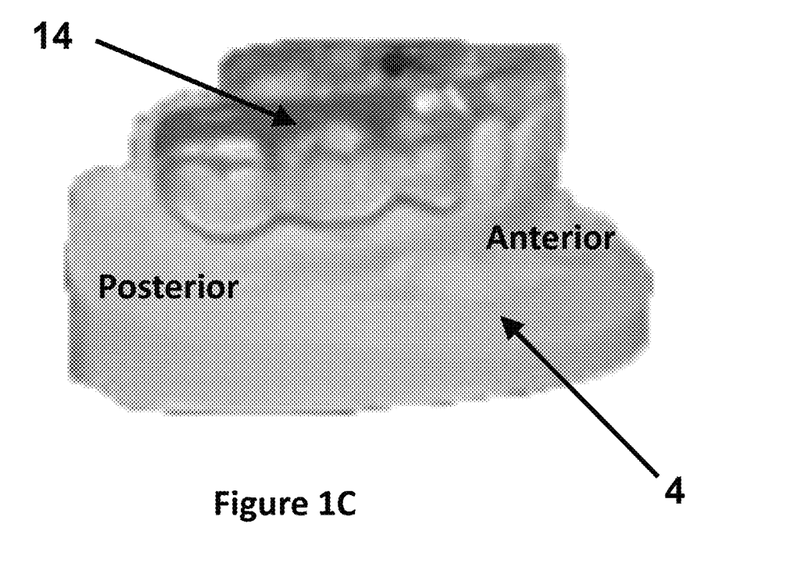
FIG. 1C is a side view of the orthopaedic/orthodontic device shown in FIG. 1A.

Illustrated in FIGS. 1A to 1C is an orthopaedic/orthodontic device 10 moulded for a maxilla 4 of a patient 2.

The orthopaedic/orthodontic device 10 according to this embodiment has a platform 14, palatal side wall 16 and buccal side wall 18. The platform 14 of the orthopaedic/orthodontic device is contoured for contact with teeth 8 of the patient 2 and includes a curved upper portion shaped for being located inside the arch of the teeth 8 of the maxilla 4 of the patient 2 and positioned in a roof of the patient's mouth. The orthopaedic/orthodontic device also comprises a hole 24 in the upper curved portion 20 of the platform 14 to accommodate the patient's tongue. The hole 24 may myofunctionally draw the tongue forward to encourage proper swallowing patterns, activate the diaphragm to work, encourage nose breathing, relax the lower chin and tighten upper lip muscles. The hole 24 may be made smaller or larger as required. In addition, the anterior portion of the platform 14 is open with substantially no side walls to allow for expansion of the pre-maxilla. The orthopaedic/orthodontic device also comprises a split 28 in the centre of the anterior portion. This allows for expansion of the orthopaedic device.

The platform 14 has a posterior and anterior bite plane 22 which may be formed so as to be either flat or sloped in order to bring the wearer's mandible forward when the mandible is occluding in the bite plane 22 and to relax the wearer's chin and neck muscles. The platform 14 is formed according to the shape desired to be given to the wearer's jaw. The anterior bite plane helps to put the wearer's teeth together so that there is no deep bite, to unwrap the mandible and so that the right amount of bottom teeth is showing. FIG. 1C shows that the platform 14 will be thicker in the posterior region and thinner toward the anterior region.

Figure 6A:
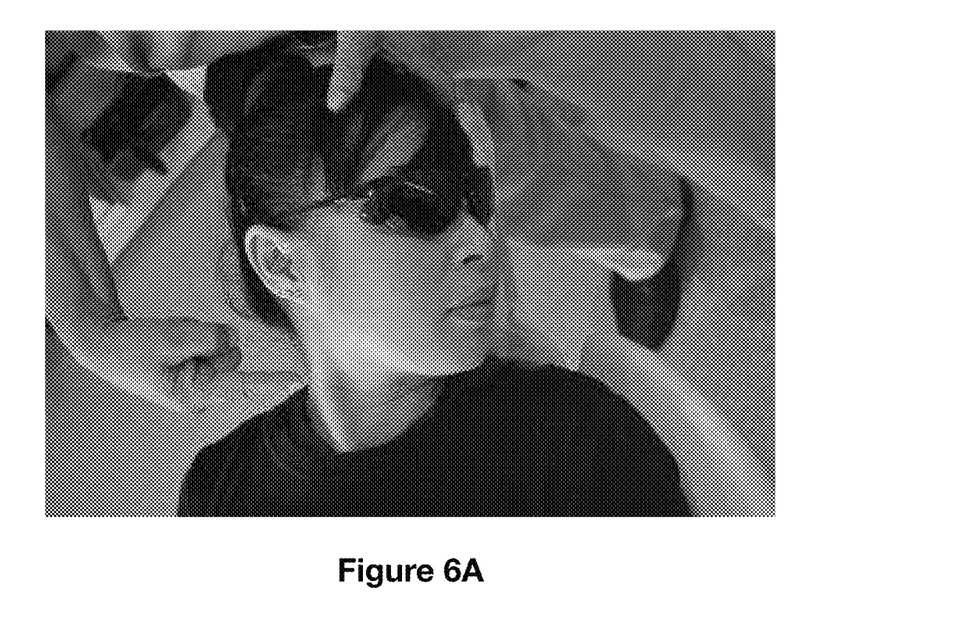
FIG. 6A shows a first test that may be conducted on a patient to determine the correct height of the orthopaedic/orthodontic device.
Figure 6B:
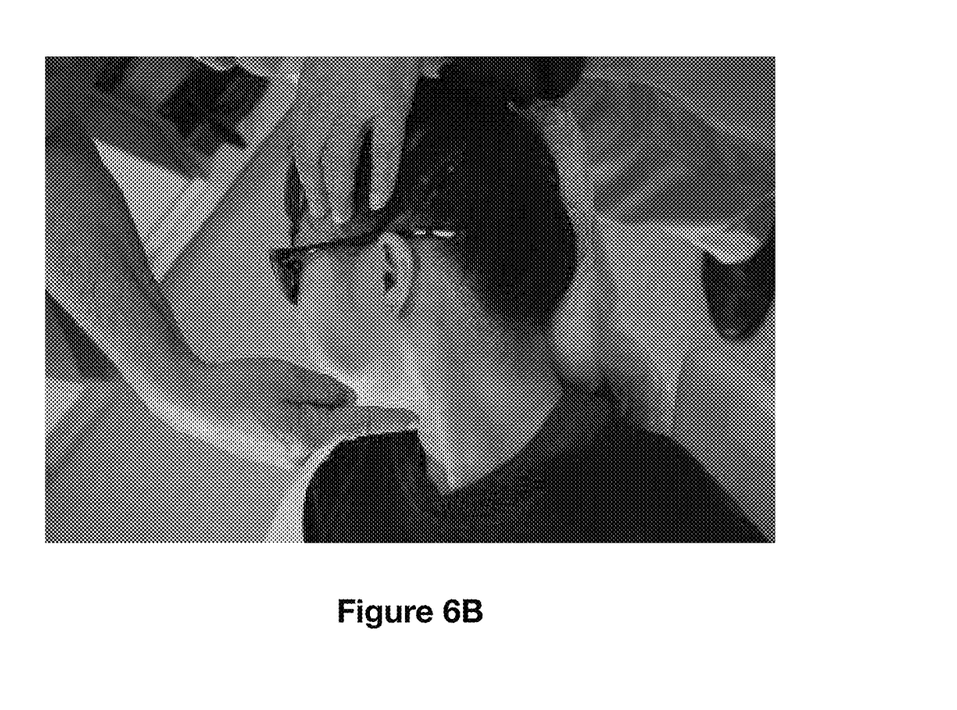
FIG. 6B shows a second test that may be conducted on a patient to determine the correct height of the orthopaedic/orthodontic device.
Figure 6C:
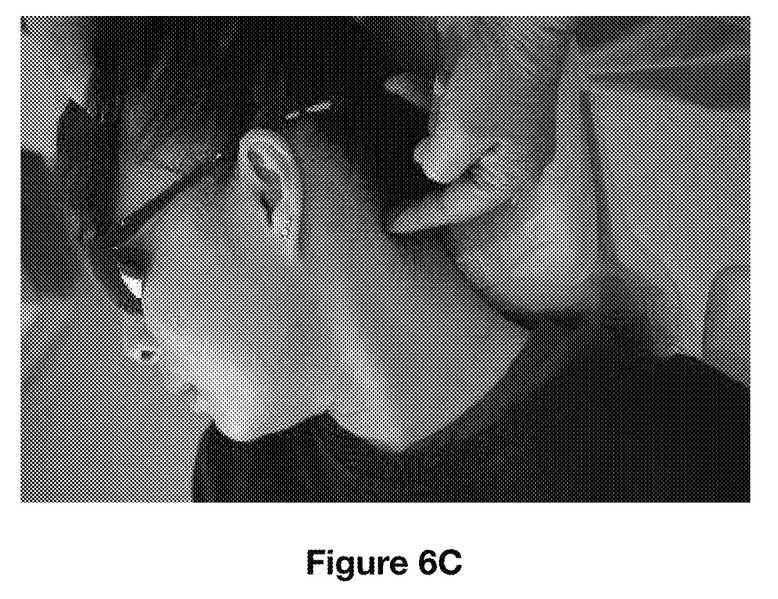
FIG. 6C shows a third test that may be conducted on a patient to determine the correct height of the orthopaedic/orthodontic device.
Figure 6D:
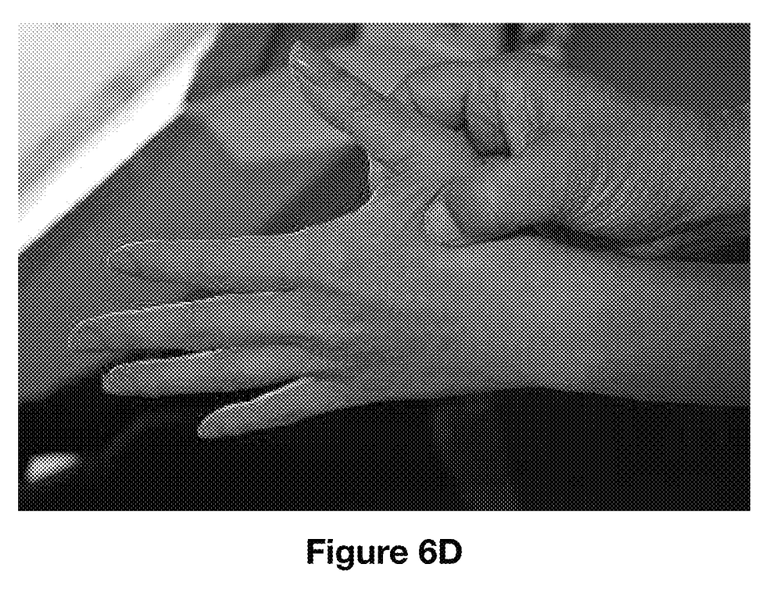
FIG. 6D shows a fourth test that may be conducted on a patient to determine the correct height of the orthopaedic/orthodontic device.
Figure 6E:
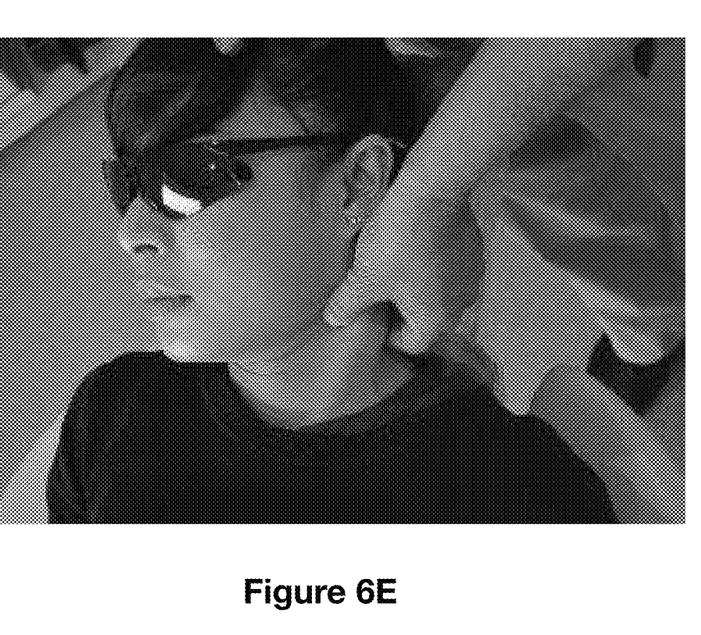
FIG. 6E shows a fifth test that may be conducted on a patient to determine the correct height of the orthopaedic/orthodontic device.
Figure 6F:
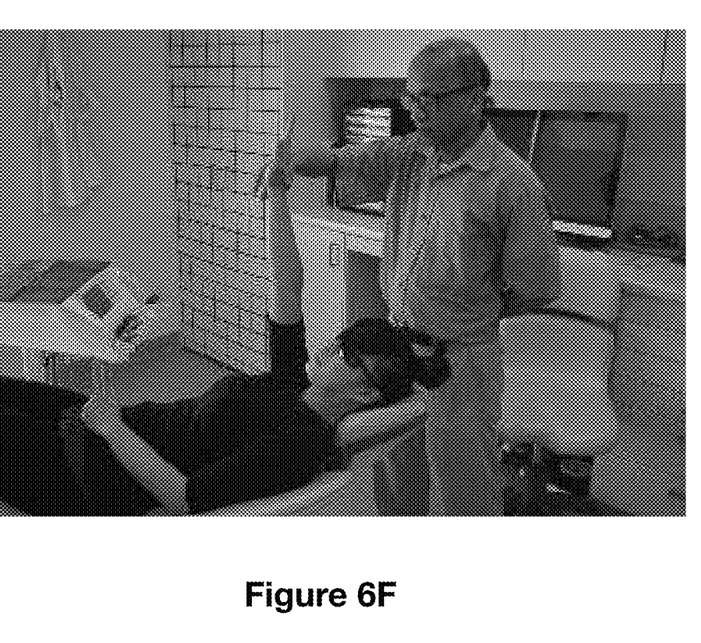
FIG. 6F shows a sixth test that may be conducted on a patient to determine the correct height of the orthopaedic/orthodontic device.

The platform 14 is manufactured such that it produces increased vertical spacing 15 between the jaws 4, 6 of the patient (also referred to as a vertical bite) of up to 20 mm when the jaws 4, 6 are occluded with the orthopaedic/orthodontic device 10 fitted. Preferably, the spacing 15 is approximately 10 mm, but may be between 0 and 5 mm, between 5 and 15 mm or between 15 and 20 mm. The size of the required spacing is determined based on a number of factors, including head rotation, pain, strength, muscle resistance, jaw motion and patient breathing. These factors may be measured using the four tests shown variously in FIGS. 6A to 6F. FIGS. 6A and 6B show a head rotation test, whereby the head is rotated to determine the maximum rotation. FIGS. 6C and 6D show a muscle pain relief test involving applying pressure to key areas of the body. FIG. 6E shows a squeeze test. The squeeze test is conducted by placing popsicle sticks between the teeth of the upper maxilla and lower mandible. The suspect muscles of the patient are then pinched or squeezed to determine the absence of pain or discomfort. FIG. 6F shows a muscle resistance test. The patient holds their hand vertically up and resist the pushing of one hand or one finger according to the case. An increase in strength or absence of pain in a trigger point in the neck or shoulders indicates a good position of mandible in relation to maxilla.

Further testing of the correct vertical separation of the jaws 4, 6 may be conducted by inserting popsicle sticks between anterior teeth 8, 12 of the maxilla and mandible and then examining the patient for changes in pain and/or breathing.

A jaw position that results in favourable readings from one or more of these tests is then chosen as the preferred vertical spacing 15 between the jaws.

The device is also provided with a 2-way expansion screw mechanism 26 for enlarging the maxilla of the wearer in left and right directions. The expansion screw 26 is provided with apertures for receiving a tool (not shown) which is used by a dentist/orthodontist or patient to adjust the effective size of the orthopaedic/orthodontic device 10. The orthopaedic/orthodontic device 10 is able to expand in response to adjustment of the expansion screw 22. The expansion screw mechanism is not adjusted as in normal orthopaedics/orthodontics, but done in a similar fashion as to cases involving a growing child. The adjustment is minimal such that the fluid in the periodontal ligament is not forced away, but instead the periodontal ligament is gently compressed to swell the bone and stimulate growth. During treatment, the bone and the teeth move at the same time and the growth of the mandible and maxilla is happening at the same rate respectively. The orthopaedic/orthodontic device 10 may also instead comprise a three-way expansion screw.

The orthopaedic/orthodontic device 10 is fitted to the jaw of the patient, so that it feels it is expanding slightly, but not contracting. The fit of the appliance must be neutral, so it is not jammed when fitted and can be removed by the patient without difficulty, while at the same time being firm and not falling out. This is to avoid cranial jamming.

In order to manufacture the orthopaedic/orthodontic device 10 described above, impressions of the patient's jaws 4, 6 are taken, and models of the jaws are made from these impressions. It is desirable for the impressions and models to have a high degree of accuracy such that the appliance can be manufactured to fit well and to work effectively. The impressions may be made in alginate, rubber or other suitable material known in the art. Alternatively, a mould may be formed from a digital scan of the patient's mouth.

The impressions should include detail extending back to the rearmost teeth, including most of the palate. Lower impressions require as much of the lingual plate as possible. When impressions are taken using alginate, they must be poured before they dry out. Models can be poured up to the next day if kept wet. Rubber impressions can also produce suitable results. During the process of taking impressions and after selecting a suitable tray for supporting the impression material, the loaded impression should initially be pressed in backwards. This will avoid gagging the patient, and also prevent forcing the material to the back of the throat. Staff should ensure a good mixture, which is not too runny. The impressions are taken when the midlines of jaws 4, 6 are aligned and the correct vertical spacing between the jaws 4, 6, as discussed above, is achieved.

The orthopaedic/orthodontic device 10 is then preferably formed substantially from heat cured acrylic, but may be formed from other suitable materials known by persons skilled in the art.

Another method of production through the laboratory or trained technician is CAD (Computer Aided Design) and CAM (Computer Aided Manufacture) where appliances are milled from an acrylic blank.

In alternative examples of the orthopaedic/orthodontic device 10, the orthopaedic/orthodontic device may further comprise wires, springs and/or further adjustment mechanisms. Illustrated in FIGS. 2A to 2F are orthopaedic/orthodontic devices comprising various wire configurations to improve the efficacy of the orthopaedic/orthodontic device. The orthopaedic/orthodontic devices of FIGS. 2A to 2D have platforms, whereas the orthopaedic/orthodontic devices of 2E to 2F do not have platforms. The inclusion of wire into the orthopaedic/orthodontic device 10 may provide additional flexibility in the fit of the appliance and scope for adjustment.

Figure 2A:
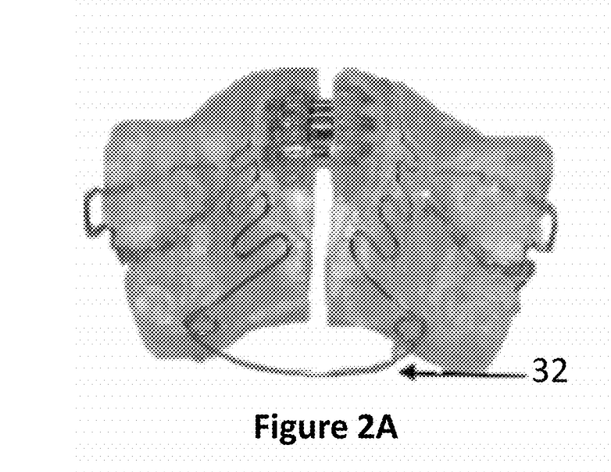
FIG. 2A is an alternative orthopaedic/orthodontic device.

Shown in FIG. 2A is the under surface of the orthopaedic/orthodontic device 10 comprising a single anterior palatal spring 32 which is 0.6 mm thick, and which pushes against the teeth in the anterior region.

Figure 2B:
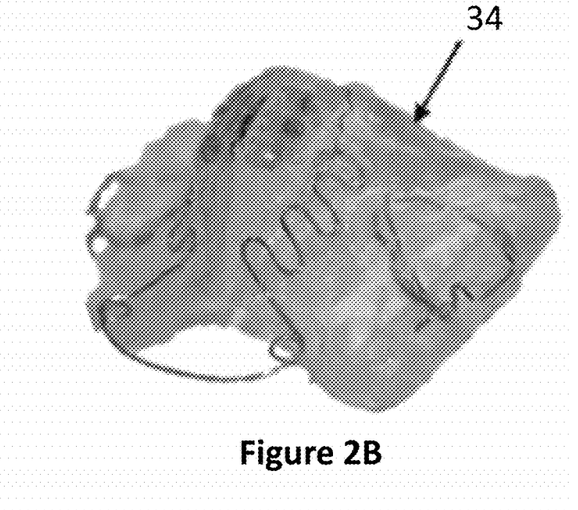
FIG. 2B is an alternative orthopaedic/orthodontic device.

FIG. 2B shows that the orthopaedic/orthodontic device has palatal relief 34.

Figure 2C:
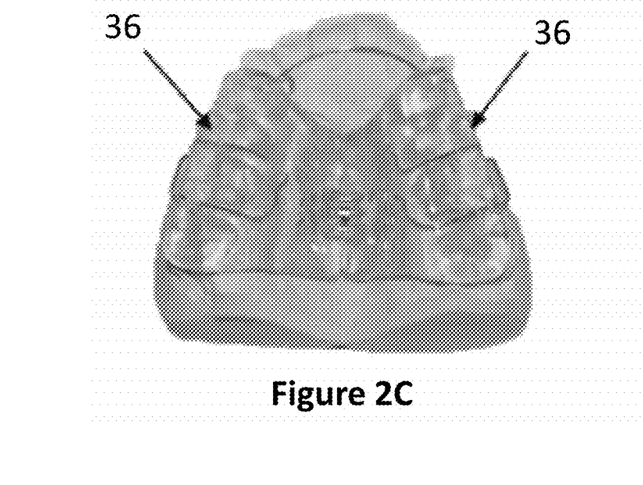
FIG. 2C is an alternative orthopaedic/orthodontic device.

FIG. 2C shows that the top of the orthopaedic/orthodontic device has an occlusal platform 36 over the teeth that occlude with the lower teeth on both sides.

Figure 2D:
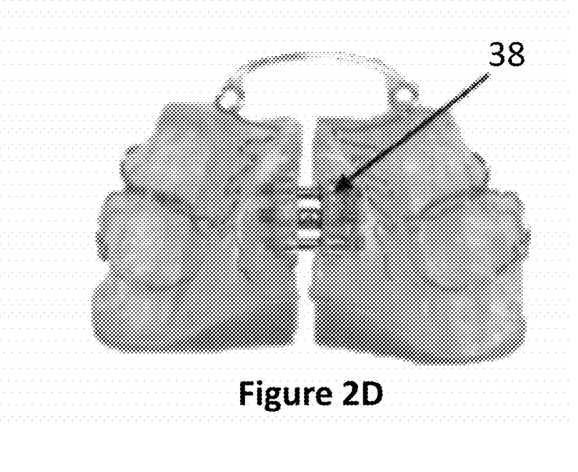
FIG. 2D is an alternative orthopaedic/orthodontic device.

FIG. 2D shows the bottom view of the orthopaedic/orthodontic device which has a 2-way screw 38 that is expanded.

Figure 2E:
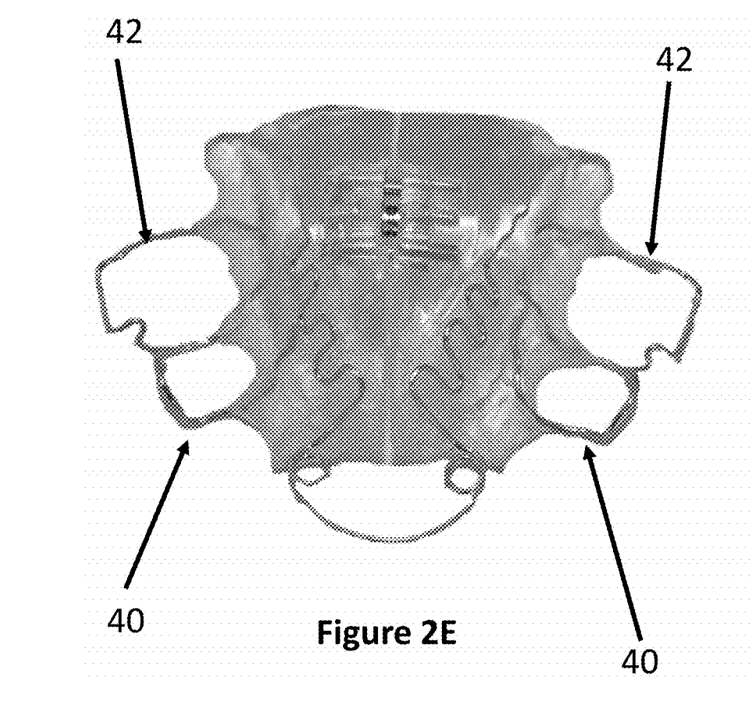
FIG. 2E is an alternative orthopaedic/orthodontic device.
Figure 2F:
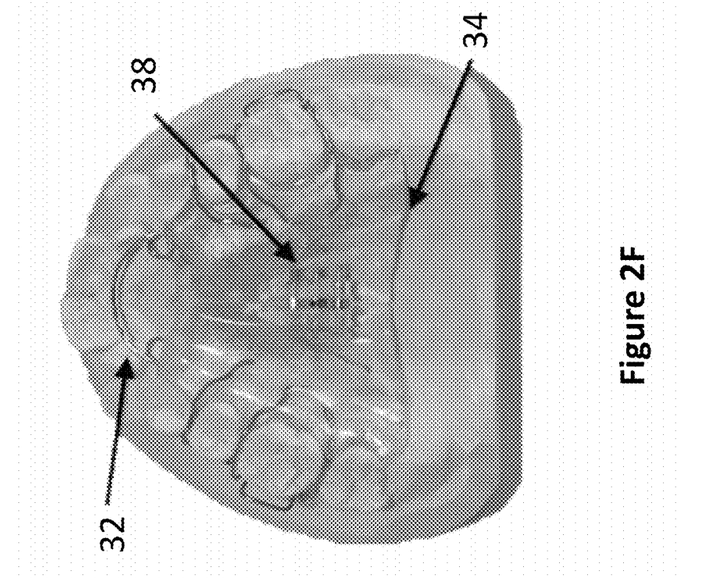
FIG. 2F is an alternative orthopaedic/orthodontic device.

FIGS. 2E and 2F are an example of the orthopaedic/orthodontic device with no platform. This type orthopaedic/orthodontic device is very versatile for younger children and older adults. This orthopaedic/orthodontic device also comprising of a single anterior palatal spring 0.6 mm thick 32. There is also a C clasp 40 on the premolar or deciduous molar on the left and right sides. There is a second Adams clasp 42 that is wrapped around the posterior molar on left and right sides. These clasps provide additional retention.

Figure 3A:
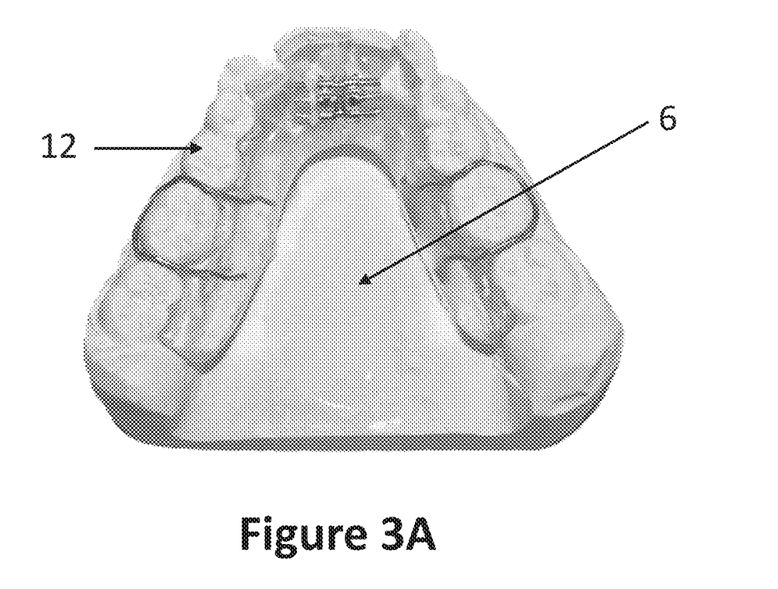
FIG. 3A shows an orthopaedic/orthodontic device fitted to a plaster cast representing the mandible of a patient together with a first wire configuration.
Figure 3B:
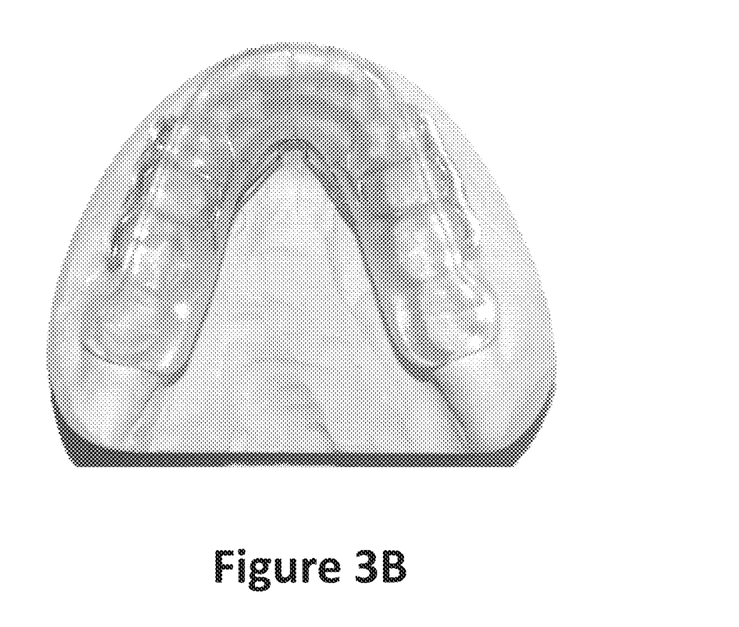
FIG. 3B shows an orthopaedic/orthodontic device fitted to a plaster cast representing the mandible of a patient together with a second wire configuration.

In yet further examples of the orthopaedic/orthodontic device, FIGS. 3A to 3B show orthopaedic/orthodontic devices which may be manufactured to be fitted to the mandible 6 of the patient 2. This alternative device may also be fitted with wires and adjustment mechanisms. For example, the orthopaedic/orthodontic devices may include wires, Adams Clasp, platforms or no platform and expansion screws.

The orthopaedic/orthodontic devices may be used as part of a splint, orthopaedic/orthodontic or myofunctional appliance. The inventor has devised a method of combining these therapies together and through which developed what may be referred to commercially as the Splint, Orthopaedic, and Myofunctional Appliance (SOMA). The method disclosed herein may be used to prepare and fit a SOMA. Details of the process of applying the orthopaedic/orthodontic devices described previously are discussed below.

Basic records that may be taken before commencing treatment:
1. A CT scan (computerised tomography) is the most preferable. This is necessary in order to evaluate a patient's physical condition by checking, amongst other things, the proper functioning of their airway, TMJ (temporomandibular joint), atlas, neck and teeth.
2. If a CT scan is unavailable, an orthopantomogram (OPG) or cephalogram may be taken to identify any abnormalities, such as missing or abnormally positioned teeth, or fractures etc.
3. Study models and photographs—these may be used to monitor progress through the treatment.
4. Nutrition history.
5. A good visual inspection of the tonsils and breathing, including tonsil size (walnut, plum, olive or pea)—a gag reflex indicates inflammation of the throat, or sensitivity.
6. The range of jaw movements and measurements standard in orthodontics, and deviations including a measurement of jaw opening (jaw opening is one of the best indicators of muscle relaxation).
7. Blood tests may be necessary with some patients to see endocrine problems.
8. Medical history.
9. Importantly, the four basic tests are done and recorded with and without the orthopaedic/orthodontic device 10 on the first visit.

It may also be beneficial to advise the patient to avoid dairy, gluten, grains such as wheat, rye amongst others, and sugar. Also, thyroid over-stimulating foods such as chocolate, coffee should be avoided.

The vertical opening of the jaw that is considered normal must be at least a minimum jaw opening of 50 mm between the teeth of the mandible 6 and maxilla 4. The opening may be measured using a ruler. As jaw opening improves so does optimum function until the maximum is achieved even above 70 mm. The head may be able to be turned as shown from right shoulder to left shoulder at least 180 degrees measured from the middle of the chin to midline of shoulder in the horizontal plane. The smaller the jaw opening, the greater the TMJ, TMD, pathology and symptoms present. Symptoms that may be recorded include mood, energy levels and sleep quality.

Method of Preparation of the Orthopaedic/Orthodontic Device

After the orthopaedic/orthodontic 10 device has been fitted to a patient's jaw, it may be prepared for use to correct occlusion of the patient's jaws 4, 6. In the case of the present example, the first jaw denotes the maxilla 4 of the patient 2.

Figure 4:
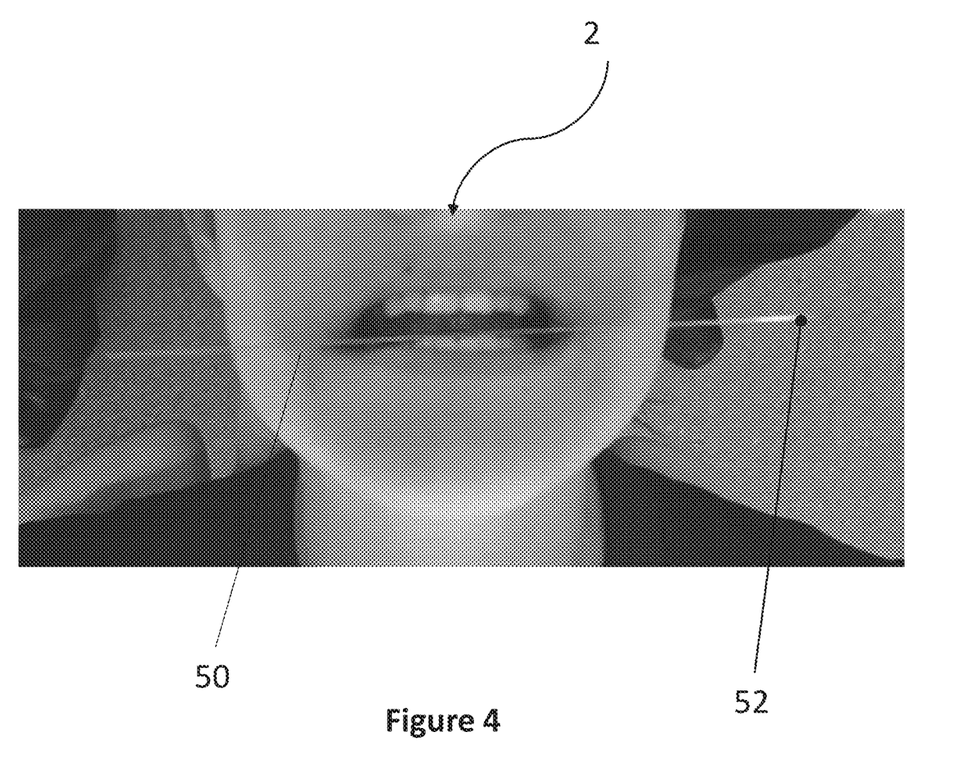
FIG. 4 shows a patient with orthopaedic/orthodontic device fitted and ruler clamped between the orthopaedic/orthodontic device and mandible of a patient.

A ruler 50 or flat paddle (not shown) is then placed flat in the patient's mouth between the anterior teeth of the maxilla 4 and mandible 6, as shown in FIG. 4. This is to determine the horizontal cant of the jaw. The side for which the end of the ruler 52 is closest to the eye is referred to as the low side and becomes the reference side 44 of the orthopaedic/orthodontic device 10. The ruler is then removed.

The contact areas between the orthopaedic/orthodontic device 10 and the teeth 12 of the opposing jaw 6 during parafunction and occlusion in a central position are then identified. Contact areas are points or regions of contact between teeth of one jaw and another surface, which may be, but is not limited to, a surface of a tooth of the other jaw or a surface of the orthopaedic/orthodontic device.

The parafunction contact areas are identified by first inserting the articulating paper into the patient's mouth between the orthopaedic/orthodontic device 10 and the teeth 12 of the opposing jaw 6 to the orthopaedic/orthodontic device 10. The articulating paper may be held using millers forceps. The patient 2 is then asked to close their mouth and horizontally translate their mandible 6 in extreme forward and backward, side-to-side and circular motions. The translations may also include other grinding motions. As the patient translates their jaw, the articulating paper will leave marks 46 ("parafunction" contact areas) on the orthopaedic/orthodontic device 10 and on the teeth 12 of the opposing jaw 6 in areas where there would have been contact between the teeth 12 and orthopaedic/orthodontic device 10 if not for the presence of the articulating paper. The articulating paper is then moved to different positions around the jaw 6 and the parafunction motions repeated to mark all areas of contact between the jaw 6 and orthopaedic/orthodontic device 10.

The articulating paper is then replaced with articulating paper of a different colour. The patient is then asked to "tap" with their jaw. This motion consists of the patient opening and closing their mouth while their jaw is in a neutral or central position. When the patient taps with their jaw, the articulating paper will leave marks corresponding to an additional set of contact areas 48 ("rest" contact areas) on the orthopaedic/orthodontic device 10 and on the teeth 12 of the second jaw 6. The articulating paper is again moved around the jaw to encompass all of the teeth 12 of the patient 2 in the marking process.

Figure 5A:
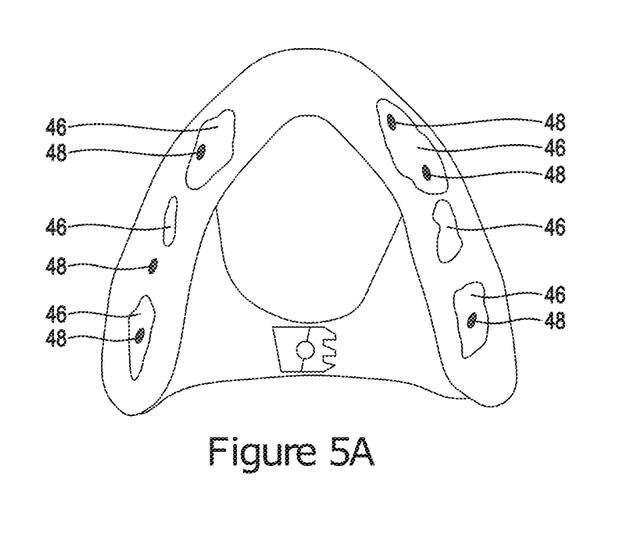
FIG. 5A is a schematic drawing showing contact area markings created on an orthopaedic/orthodontic device.
Figure 5B:
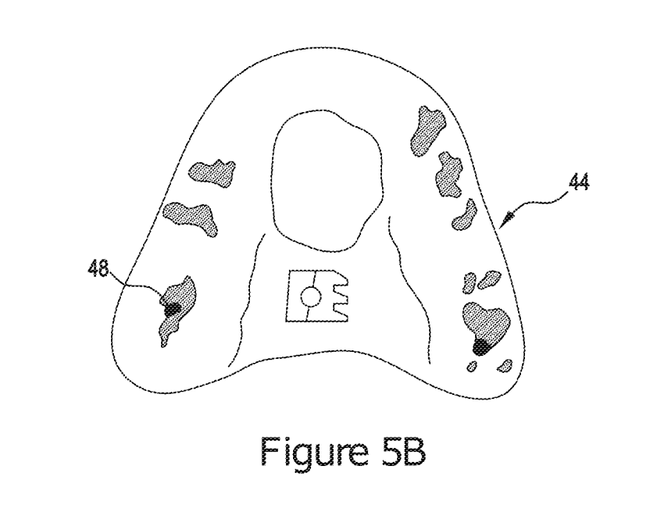
FIG. 5B shows contact area markings created after shaping, adjusting and/or trimming of the orthopaedic/orthodontic device.
Figure 5C:
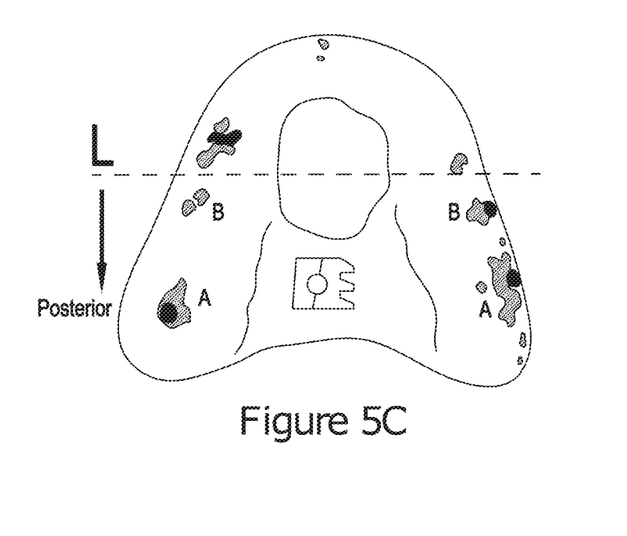
FIG. 5C shows contact area markings created after further shaping, adjusting and/or trimming of the orthopaedic/orthodontic device.

The result is that there will be two sets of marks created on the orthopaedic/orthodontic device corresponding to parafunction contact areas 46 and rest contact areas 48. Each set of contact areas is identifiable by the coloured articulating paper used to create the marks. While the parafunction contact areas 46 typically appear as smudges or areas on the orthopaedic/orthodontic device 10, as shown in FIGS. 5A to 5C, the rest contact areas 48 typically appear as dots. In FIG. 5A, parafunction contact areas 46 are shown as striped regions, while rest contact areas are shown as solid regions.

The orthopaedic/orthodontic device 10 is then removed from the patient's mouth and the contact areas 46, 48 examined. A correctly aligned jaw will have rest contact areas that are balanced on left and right side of the maxilla. A contact area is balanced if there is a contact area symmetrically located on the other side of the orthopaedic/orthodontic device 10. In FIG. 5C, it can be seen that there are two rest contact areas, A, on respective left and right sides of the orthopaedic/orthodontic device 10 which are balanced and one area, B, on the right side that is not. The rest contact areas 48 and parafunction contact areas 46 should also occur in substantially the same location. If this is the case, it will indicate that contact during horizontal translation is in the same location as contact during rest.

If the arrangement of the contact areas 46, 48 does not satisfy these two conditions, then the orthopaedic/orthodontic device 10 must be shaped, adjusted and/or trimmed. Shaping, adjusting and/or trimming is achieved by removing material from the orthopaedic/orthodontic device 10. A suitable grinding tool or other tool known in the art can be used for this purpose. The grinding tool may be a rotary grinding tool.

Where the rest contact areas 48 are not balanced on either side of the orthopaedic/orthodontic device 10, shaping, adjusting and/or trimming should first be conducted to remove material on the high side (opposed side to the reference side) of the orthopaedic/orthodontic device 10. Similarly, any area corresponding to a parafunction contact area 46 that does not align with a rest contact area 48, must also be removed.

The shaping, adjusting and/or trimming of the orthopaedic/orthodontic device 10 should be conducted in a staged manner, such that shaping is initially conducted in the posterior most region of the orthopaedic/orthodontic device 10. After shaping, adjusting and/or trimming of the orthopaedic/orthodontic device 10 in the anterior regions, the orthopaedic/orthodontic device 10 should be refitted and the contact areas 46, 48 marked again. If the posterior marks align, the process can be conducted for marks toward the anterior region of the orthopaedic/orthodontic device 10. The process is repeated until all the marks are sufficiently close to satisfying both conditions.

In FIG. 5A, there are several parafunction contact areas 46 and rest contact areas 48 shown. It can be seen that there are two pairs of rest contact areas 48 (anterior-most pair and posterior-most pair) which are balanced on both sides of the orthopaedic/orthodontic device 10. These rest contact areas 48 also coincide with parafunction contact areas 46 in these regions. However, the two remaining rest contact areas are not balanced. Thus the rest contact area on the side not being the reference side should be removed as well as all the sections of the parafunction contact areas 46 not coinciding with rest contact areas 48.

Upon shaping, adjusting and/or trimming the orthopaedic/orthodontic device 10, the process of refitting the orthopaedic/orthodontic device, identifying the contact areas 46, 48 and shaping, adjusting and/or trimming the orthopaedic/orthodontic device is repeated until the contact areas 46, 48 are sufficiently close to an aligned configuration. If removal of material from the orthopaedic/orthodontic device 10 is insufficient to relocate the contact areas, then the patient's teeth themselves may be ground to achieve the appropriate contact pattern. This may be the case for severely over erupted teeth.

There must be at least two matching rest and parafunction contact areas in the posterior region of the orthopaedic/orthodontic device. The posterior region being that behind the dashed line labelled "L" in FIG. 5C.

Figure 5D:
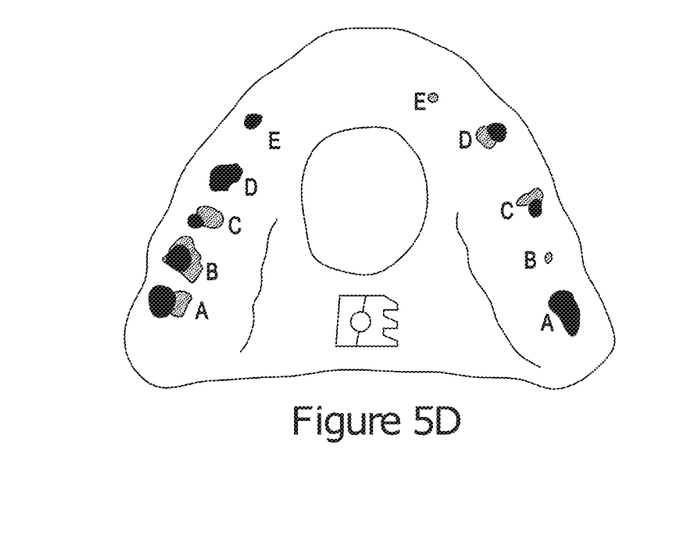
FIG. 5D shows contact area markings created after further shaping, adjusting and/or trimming of the orthopaedic/orthodontic device.

As shown in FIG. 5D, the objective is to have all the contact areas 46, 48 being in substantially the same location as a contact area of the other type and to have a substantially symmetrical arrangement of contact areas. The letters A to E marked on FIG. 5D indicate respective pairs of contact areas on left and right sides of the orthopaedic/orthodontic device 10.

Once the orthopaedic/orthodontic device 10 is prepared, the patient is to wear the orthopaedic/orthodontic device 10 at regular intervals for a set period of time. For example, the patient may wear the device nightly for three months. In some cases, the patient may also be prescribed a device without a platform (eg as shown in FIGS. 2E and 2F) to be worn during the day so as to maintain treatment without affecting speech. After which time the patient returns and the SOMA methodology is repeated to adjust the orthopaedic/orthodontic device 10 to suit the new positions of the teeth and jaw of the patient. This process is repeated for a period of a few months to a few years until a final position is reached and no further adjustments is required. The initial measurements taken, should be retaken at each adjustment of the orthopaedic/orthodontic device 10 to quantify the degree of improvement in the patient 2.

As described previously, favourable signal patterns may result from altered proprioception of the teeth perceived by the brain. The result of these favourable signal patterns may be observable by larger jaw opening width. The method described above was applied to several trial participants. At each visit the jaw opening width of the patient was recorded. The results are shown in Table 1 below, illustrating observable changes in patient's utilising the orthopaedic/orthodontic device 10 having the SOMA method applied.

TABLE 1

| | Jaw Opening Width (mm) | | | |
|---|---|---|---|---|
| Patient | Pre-Treatment | Visit 1 | Visit 2 | Visit 3 |
| 1 | 37 | 44 | 41 | 47 |
| 2 | 31 | 35 | 45 | 48 |
| 3 | 47 | 55 | 57 | — |
| 4 | 46 | 48 | 50 | 52 |
| 5 | 41 | 47 | 45 | 46 |
| 6 | 45 | 56 | 53 | 56 |
| 7 | 49 | 53 | 57 | 62 |
| 8 | 49 | 56 | 58 | 56 |

In another trial, participants provided self-assessed ratings for symptoms such as mood, energy levels and sleep quality before and throughout treatment. The ratings range from 1 to 10, with 10 signifying excellent mood, excellent energy levels and excellent sleep quality respectively. The results are shown in Tables 2-4 below.

TABLE 2

| | Energy | | |
|---|---|---|---|
| Patient | Visit 1 | Visit 2 | Visit 3 |
| 1 | 2 | — | 7 |
| 2 | 5 | 6 | 8 |
| 4 | 6 | 7 | 10 |
| 5 | 4 | 6 | 8 |
| 21 | 5 | 6 | 6 |
| 26 | 5 | 7 | 8 |

TABLE 3

| | Mood | | |
|---|---|---|---|
| Patient | Visit 1 | Visit 2 | Visit 3 |
| 2 | 5 | 7 | 9 |
| 3 | 6 | 7 | 8 |
| 4 | 6 | 8 | 8 |
| 20 | 3 | — | 10 |
| 24 | 6 | 6 | 8 |

TABLE 4

| | Sleep | | |
|---|---|---|---|
| Patient | Visit 1 | Visit 2 | Visit 3 |
| 2 | 5 | 6 | 8 |
| 4 | 4 | 8 | 10 |

TABLE 4-continued

| | Sleep | | |
|---------|---------|---------|---------|
| Patient | Visit 1 | Visit 2 | Visit 3 |
| 5 | 5 | 6 | 7 |
| 12 | 5 | — | 9 |
| 24 | 4 | 9 | 8 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

While various embodiments of the present invention have been described above, it should be understood that they have been presented by way of example only, and not by way of limitation. It will be apparent to a person skilled in the relevant art that various changes in form and detail can be made therein without departing from the spirit and scope of the invention. Thus, the present invention should not be limited by any of the above described exemplary embodiments. Although methods have been described as a sequence of steps, the steps of such methods may be performed in any order. Furthermore, steps may be performed substantially simultaneously.

The invention claimed is:

1. A method of preparing a device comprising:
   fitting the device onto a first jaw of a patient, the device having a platform contoured for contact with teeth of the first jaw;
   identifying a first set of contact areas between the device and teeth of a second jaw of the patient when the first and second jaws are moved towards each other and one jaw is translating horizontally;
   identifying a second set of contact areas between the device and teeth of the second jaw when the first and second jaws are moved towards each other in a neutral position;
   shaping, adjusting and/or trimming the device on the basis of the first or second set of contact areas to change a location of at least one contact area, wherein at least some of the shaping, adjusting and/or trimming of the device comprises shaping, adjusting and/or trimming the device on the basis of the second set of contact areas to change a location of at least one contact area of the second set of contact areas; and
   repeating the preceding steps to bring the contact areas to or towards a desired configuration.

2. The method according to claim 1, wherein at least some of the shaping, adjusting and/or trimming of the device comprises shaping, adjusting and/or trimming the device on the basis of the first set of contact areas to change a location of at least one contact area of the first set of contact areas.

3. The method according to claim 1, wherein the horizontal translation includes one or more of forward and backward, side-to-side and circular motions.

4. The method according to claim 1, wherein at least some of the shaping, adjusting and/or trimming of the device is based on whether the first set of contact areas are balanced on left and right sides of the device.

5. The method according to claim 1, wherein at least some of the shaping, adjusting and/or trimming of the device is based on whether the second set of contact areas are balanced on left and right sides of the device.

6. The method according to claim 1, wherein at least some of the shaping, adjusting and/or trimming of the device is based on whether the first and second sets of contact areas occur in similar locations.

7. The method according to claim 6, wherein the contact areas are at the desired configuration when each of the first set of contact areas occurs in a similar location to a contact area of the second set of contact areas and the contact areas are balanced on left and right sides of the device.

8. The method according to claim 1, further comprising shaping, adjusting and/or trimming at least one of the patient's teeth to change a location of at least one contact area.

9. The method according to claim 1, wherein the first and second sets of contact areas are identified using coloured articulating paper and the first set of contact areas is identified using articulating paper of a different colour to articulating paper used to identify the second set of contact areas.

10. The method according to claim 1, wherein the shaping, adjusting and/or trimming of the device is performed by using a rotary cutting tool.

11. The method according to claim 1, wherein the device is shaped, adjusted or trimmed to change the location(s) of posterior contact area(s) prior to shaping, adjusting and/or trimming the device to change the location(s) of one or more anterior contact area(s).

12. The method according to claim 1, wherein the device, prior to any shaping, adjusting and/or trimming step, is formed in accordance with the patient's bite impression.

13. The method according to claim 12, wherein the bite impression is made in alginate or rubber.

14. The method according to claim 12, further comprising forming the device around a mould of the bite impression.

15. The method according to claim 1, further comprising taking one or more measurements of a degree to which the patient's head turns left and right, a deviation of the midlines of the first and second jaws, height of jaw opening between teeth and a length of a protrusion forward of the mandible in relation to a patient's maxilla in translation to determine whether the patient requires tooth or jaw correction and to monitor changes to patient physiology as the patient uses the device.

16. A device prepared according to the method of claim 1.

17. The device according to claim 16, wherein the device is made from acrylic.

18. The device according to claim 17, wherein the acrylic is heat cured high quality acrylic with no monomer.

19. The device according to claim 16, further comprising a two-way or three-way expansion screw configured to adjust the size of the device.

20. The device according to claim 16, further defining a hole in the anterior palatal area behind a patient's front teeth in use to accommodate the patient's tongue for ease of speech.

21. The device according to claim 16, wherein the anterior portion of the device is open.

22. The device according to claim 16, wherein the device results in a vertical separation of the jaws of the patient or bite of up to 20 mm.

23. The device according to claim 16, wherein the device results in a vertical separation of the jaws of the patient or bite of between 5 and 15 mm.

24. The device according to claim 16, wherein the device results in a vertical separation of the jaws of the patient or bite of approximately 10 mm.

25. A method of providing orthopaedic care, the method comprising using the device of claim 16 for the provision of orthopaedic care.

* * * * *